(12) United States Patent
Boström

(10) Patent No.: US 12,115,361 B2
(45) Date of Patent: Oct. 15, 2024

(54) SAFETY CAP

(71) Applicant: SHL MEDICAL AG, Zug (CH)

(72) Inventor: Anders Boström, Ingarö (SE)

(73) Assignee: SHL Medical AG, Zug (CH)

( * ) Notice: Subject to any disclaimer, the term of this patent is extended or adjusted under 35 U.S.C. 154(b) by 589 days.

(21) Appl. No.: 16/972,510

(22) PCT Filed: Jun. 28, 2019

(86) PCT No.: PCT/EP2019/067426
§ 371 (c)(1),
(2) Date: Dec. 4, 2020

(87) PCT Pub. No.: WO2020/015985
PCT Pub. Date: Jan. 23, 2020

(65) Prior Publication Data
US 2021/0268202 A1    Sep. 2, 2021

(30) Foreign Application Priority Data

Jul. 20, 2018  (EP) .................................... 18184846
Jan. 8, 2019  (EP) .................................... 19150778

(51) Int. Cl.
*A61M 5/32* (2006.01)

(52) U.S. Cl.
CPC ........ *A61M 5/3213* (2013.01); *A61M 5/3202* (2013.01)

(58) Field of Classification Search
CPC .. A61M 5/3202; A61M 5/3205; A61M 5/321; A61M 5/3213; A61M 5/3243; A61M 5/3245
See application file for complete search history.

(56) References Cited

U.S. PATENT DOCUMENTS

2007/0250016 A1    10/2007  Pech et al.

FOREIGN PATENT DOCUMENTS

| WO | 2012/103140 A1 | 8/2012 |
| WO | 2017/102175 A1 | 6/2017 |
| WO | 2017/158805 A1 | 9/2017 |

OTHER PUBLICATIONS

International Search Report and Written Opinion for Int. App. No. PCT/EP2019/067426, mailed Oct. 1, 2019.

*Primary Examiner* — Shefali D Patel
(74) *Attorney, Agent, or Firm* — McDonnell Boehnen Hulbert & Berghoff LLP

(57) ABSTRACT

A protective cap is presented for releasable connection to a medicament delivery device, where the protective cap has openings in a proximal area for forming air passages through the protective cap.

13 Claims, 11 Drawing Sheets

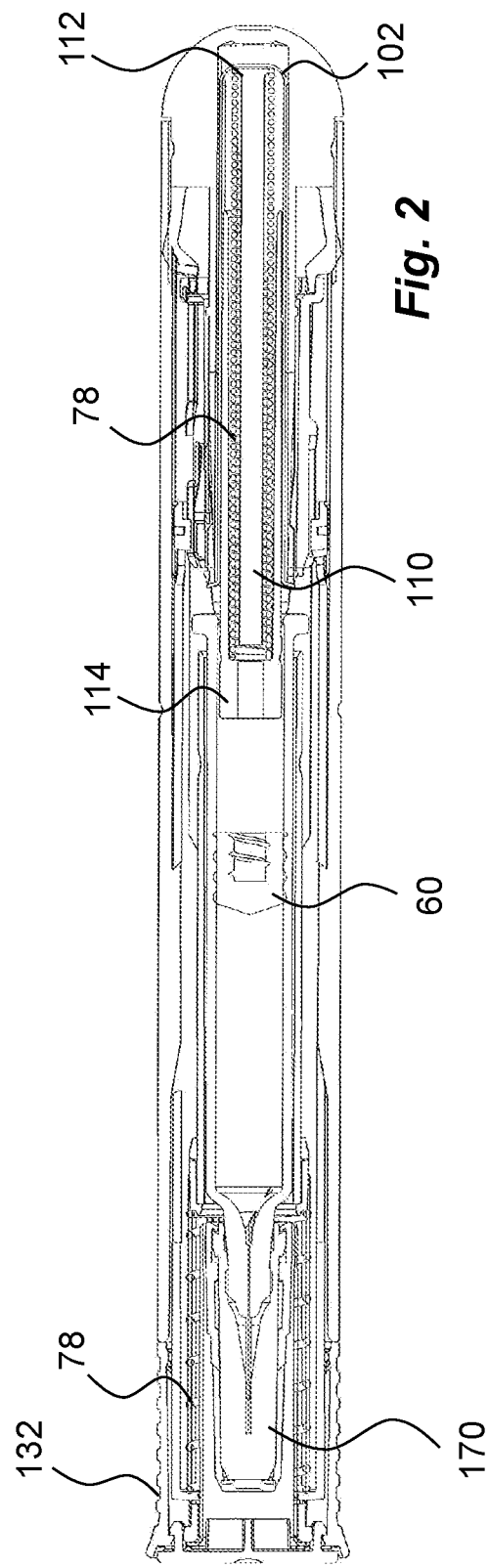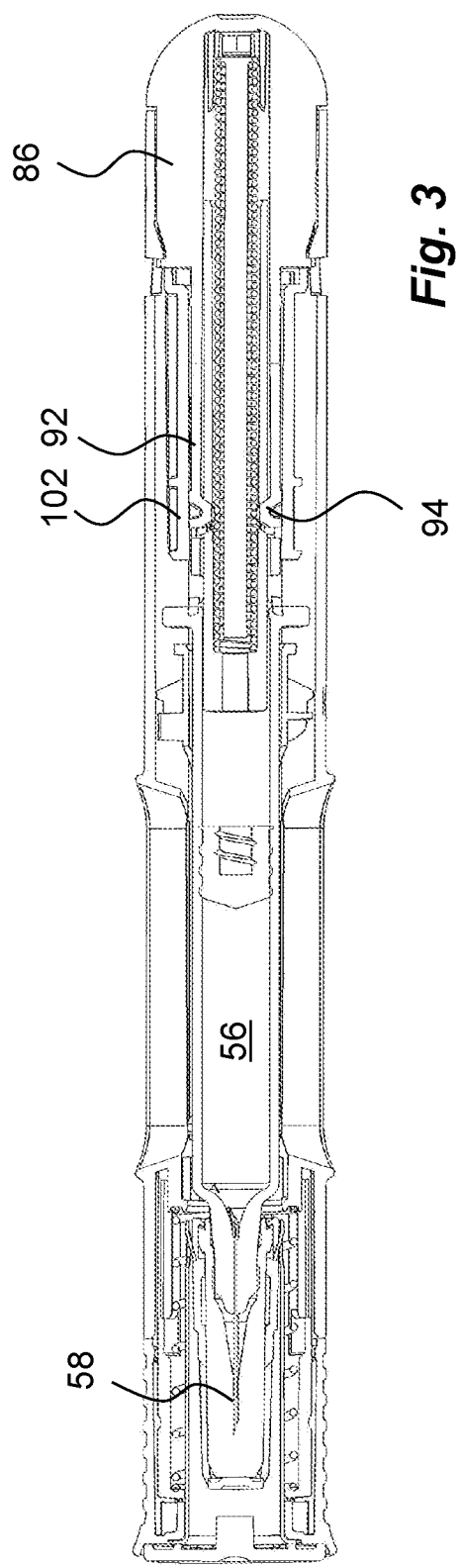

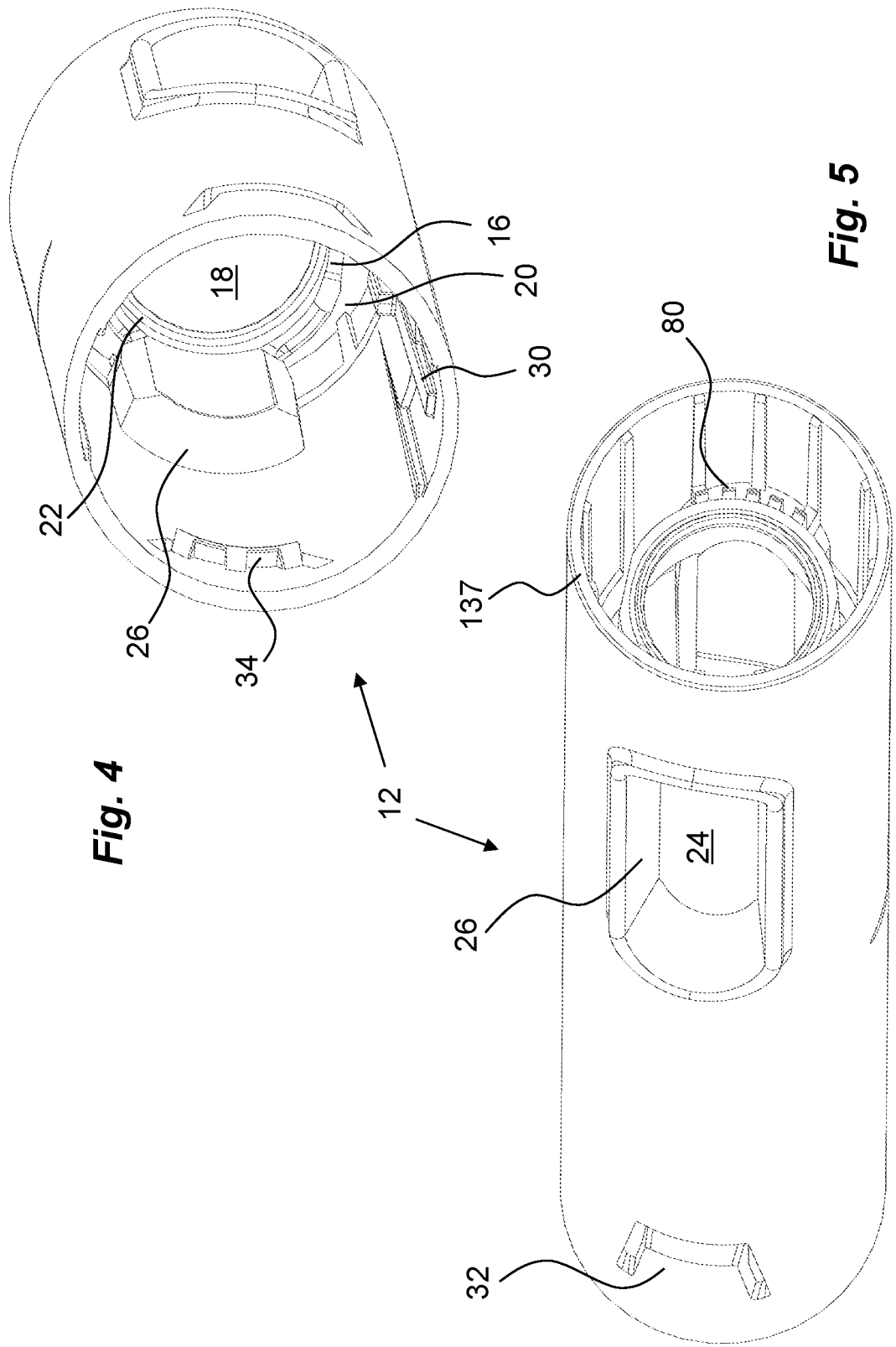

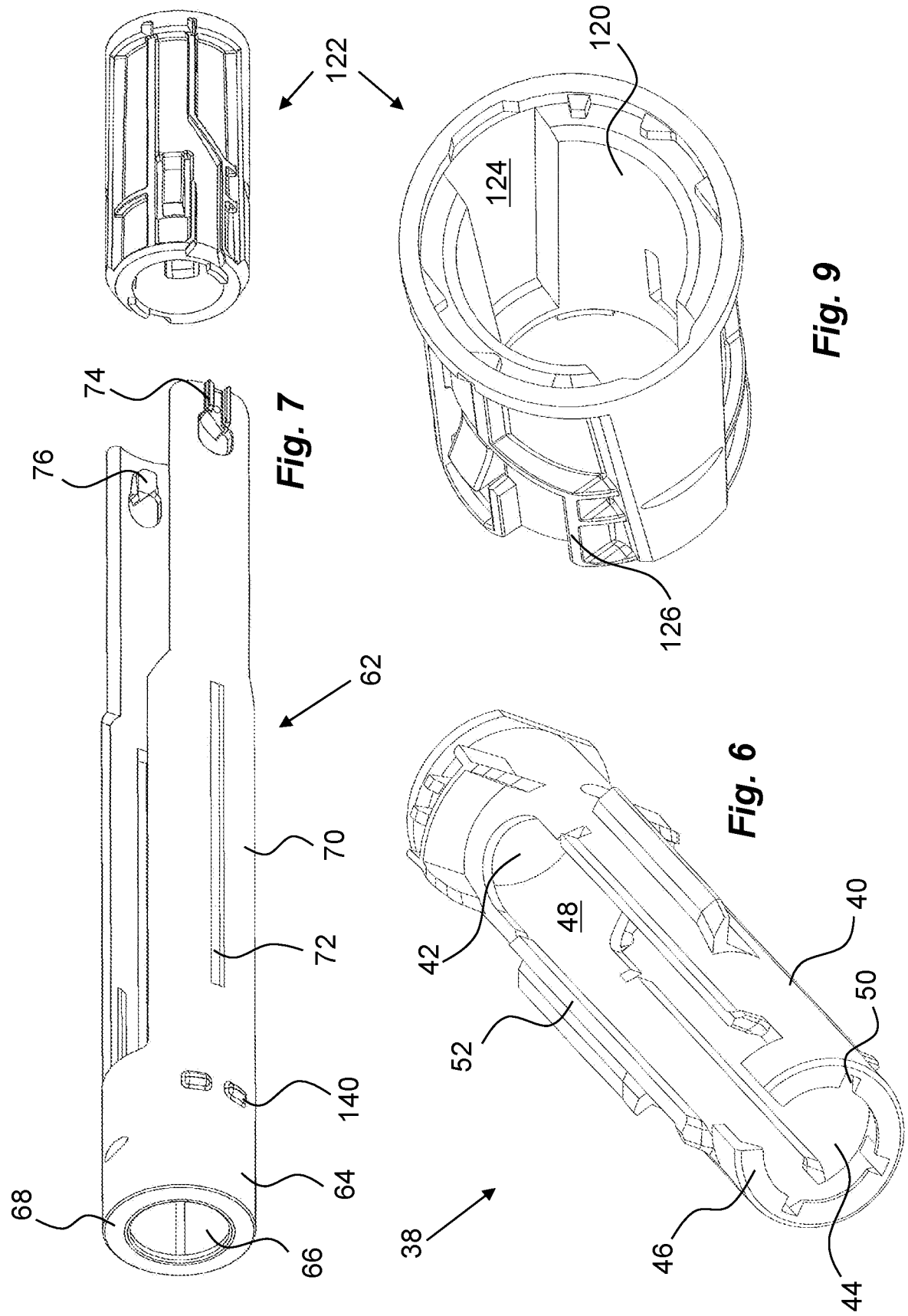

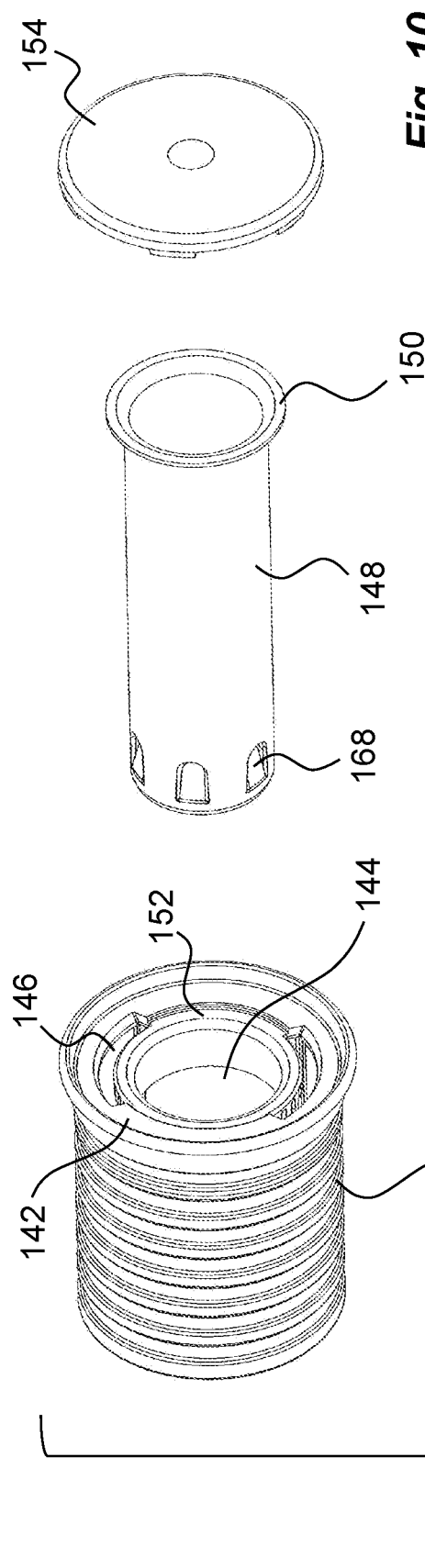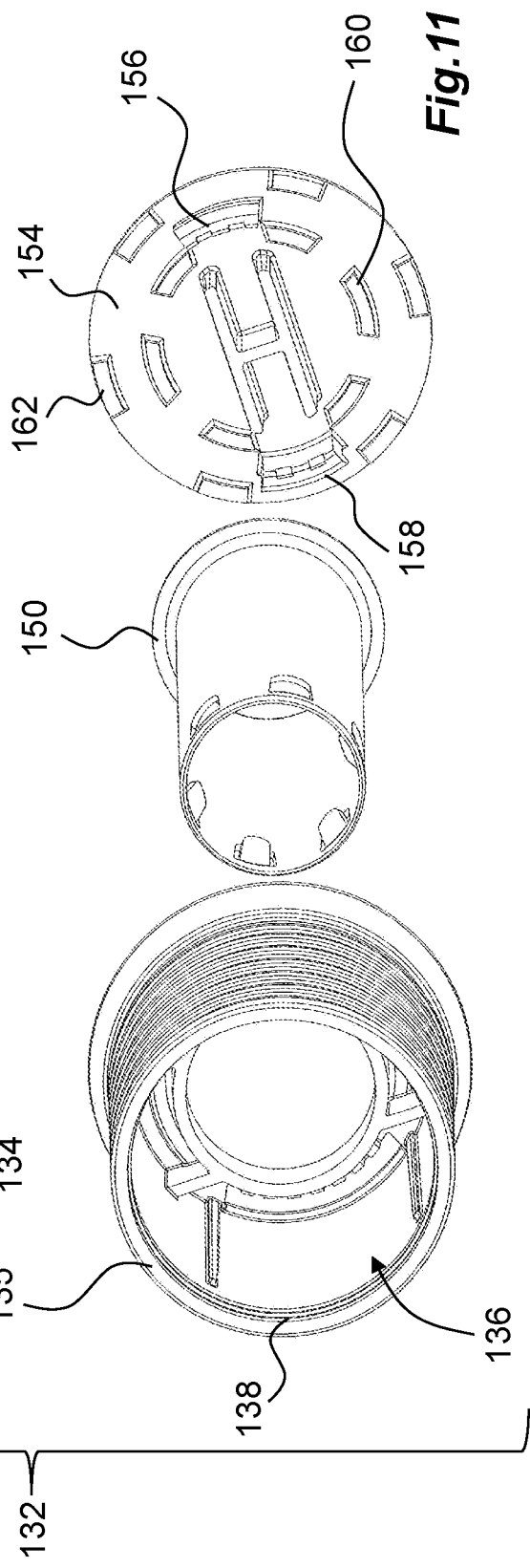

SAFETY CAP

CROSS REFERENCE TO RELATED APPLICATIONS

The present application is a U.S. National Phase Application pursuant to 35 U.S.C. § 371 of International Application No. PCT/EP2019/067426 filed Jun. 28, 2019, which claims priority to European Patent Application No. 18184846.6 filed Jul. 20, 2018, and European Patent Application No. 19150778.9 filed Jan. 8, 2019. The entire disclosure contents of these applications are herewith incorporated by reference into the present application.

TECHNICAL AREA

The present application relates to a medicament delivery device comprising a safety cap that on the one hand protects a dose delivery member of the medicament delivery device and on the other hand removes protective elements surrounding a medicament delivery member of the medicament delivery device.

BACKGROUND

A large number of medicament delivery devices on the market and developed during the last 20 years are arranged with a protective safety cap at the proximal end thereof that on the one hand protect the proximal end of the medicament delivery device, which proximal end is arranged with a dose delivery member such as an injection needle. The injection needle for instance has to be kept sterile before use, whereby it is surrounded by a covering material such as a sheath of e.g. rubber, creating a so called flexible needle shield or FNS. Further developments in that regard are the so called rigid needle shields or RNS's that have an outer shell of a more rigid material surrounding the flexible inner sheath. The main purpose in any event is to keep the injection needle protected and sterile.

The protective safety cap on the other hand usually has two functions, to protect the medicament delivery member and other elements at the proximal end of the medicament delivery device and on the other hand provide an aid for removing the medicament delivery member shield when the medicament delivery device is to be used. It is designed to facilitate for a user to pull off the protective safety cap and at the same time the medicament delivery member shield.

Even if the protective safety cap is necessary for the medicament delivery device, it is a component that can cause dangerous situations. This can for example be the case if for example a child gets hold of a removed protective safety cap and puts it in the mouth. The safety cap is too large to be swallowed but may cause the risk of suffocation if it is stuck in the mouth.

There is thus a need for minimizing the risk of suffocation if the safety cap is accidentally put in the mouth.

SUMMARY

In the present disclosure, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

The aim of the present application is to remedy the drawbacks of the state of the art devices. This aim is solved by a protective cap arrangement comprising at least one opening or a plurality of the openings in the proximal area of the protective cap for forming an air passage through the protective cap forming a subject of the independent claim. The preferred embodiments of the present application form the subjects of the dependent claims.

According to one aspect, a protective cap releasably connected to a medicament delivery device, can comprise one or a plurality of openings in the proximal area of the protective cap for forming air passage or passages through the protective cap. With this solution, the risk of suffocation if for example a child puts the protective safety cap in the mouth is greatly reduced, because the air passages will ascertain that it is still possible to breath even with the safety cap in the mouth.

The protective cap may comprise a generally tubular body and a lid attached to the proximal end, and spacers arranged between the body and the lid for creating the air passages. This is an easy way to create the desired air passages. Further, the diameter of the lid may be chosen such in relation to a proximal edge of the body that gaps are created around the circumference of the lid.

In order to attach the lid to the body, the lid may be arranged with distally directed arms, which arms are arranged with ledges wherein the arms are designed to fit into openings of the body and the ledges will snap around edges of the openings. This provides a fast and uncomplicated assembly process. In this regard, the arms may be arc-shaped and provided with radially outwardly directed ledges, and that the openings are arc-shaped. Further, the body may be arranged with an end wall in which the openings are arranged.

As a further feature, the protective cap may comprise a medicament delivery member shield remover, attached to the body and held in position by the lid. In this regard, the lid may further be arranged with a number of distally directed protrusions or ledges which are to be in contact with a ledge of the medicament delivery member shield remover, holding it in place.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which FIG. 2 is a cross-sectional view of the medicament delivery device of FIG. 1, FIG. 3 is a cross-sectional view of the medicament delivery device of FIG. 1, FIG. 4 is a detailed view of components comprised in the medicament delivery device of FIG. 1, FIG. 5 is a detailed view of components comprised in the medicament delivery device of FIG. 1, FIG. 6 is a detailed view of components comprised in the medicament delivery device of FIG. 1, FIG. 7 is a detailed view of components comprised in the medicament delivery device of FIG. 1, FIG. 9 is a detailed view of components comprised in the medicament delivery device of FIG. 1, FIG. 10 is a detailed view of components comprised in the medicament delivery device of FIG. 1, FIG. 11 is a detailed view of components comprised in the medicament delivery device of FIG. 1.

DETAILED DESCRIPTION

Figure 1:
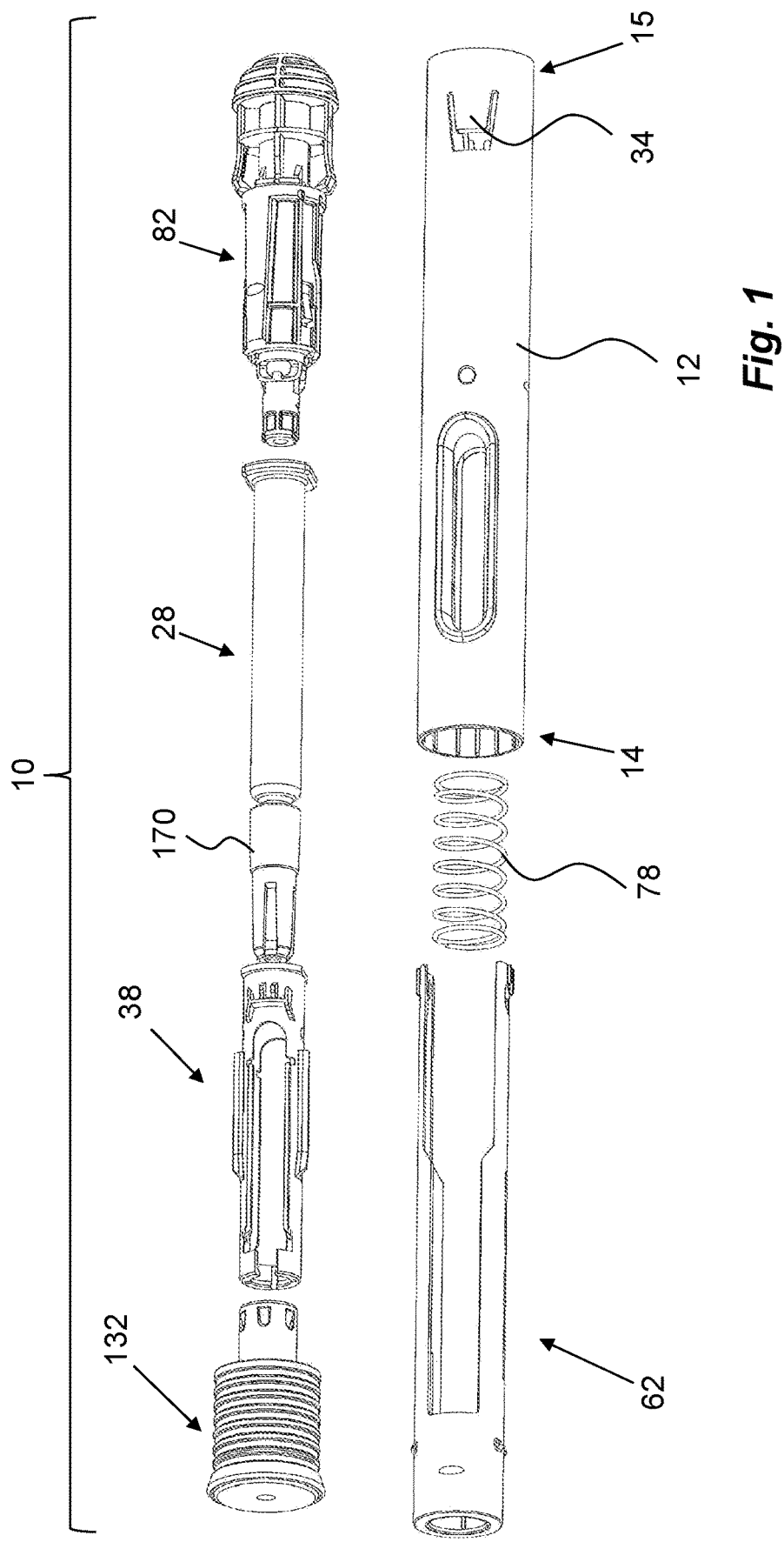
FIG. 1 is an exploded view of a medicament delivery device comprising a protective cap according to the application.

The medicament delivery device 10 shown in the drawings comprises a generally tubular housing 12 having a proximal end 14 and a distal end 15. Inside the housing a generally transversal wall 16 is arranged, FIG. 4, which wall 16 is provided with a central passage 18. Cut-outs 20 are further arranged on opposite sides of the passage 18. A seat 22 is surrounding the passage 18. Further generally rectangular windows 24 are arranged in the housing, which windows 24 are arranged with inwardly directed wall sections 26. The proximal parts of the wall sections 26 are attached to or form part of the transversal wall 16. Further, a number of longitudinally extending ribs 30 are arranged on the inner surface of the housing, having inwardly directed protrusions 32 at the proximal end thereof, the function of which will be described below. Moreover, at the distal area of the housing generally radially flexing tongues 34 are arranged, which tongues 34 are arranged with inwardly extending ledges 36 at their free ends.

Inside the housing a medicament container holder 38 is arranged coaxial. The medicament container holder 38 comprises a generally elongated tubular body 40 having a distal passage 42 and a proximal passage 44. The proximal passage 44 is arranged with an inwardly directed ledge 46 stretching around the circumference. The body 40 is arranged with two elongated slits 48 on opposite sides of the body. One of the slits 48 extends all the way to the proximal end, connecting the slit with the proximal passage, creating a C-shaped appearance when viewing in the distal direction. The circumferential ledge is further arranged with a number of cut-outs 50, three in the embodiment shown, for providing flexibility of the proximal part of the medicament container holder as will be described. The longitudinal sides of the slits 48 are arranged with outwardly directed ledges 52, which ledges 52 are designed to be in contact with inwardly surfaces 54 surrounding the windows 24 of the housing, for providing orientation and rotational fixation in relation to the housing. The medicament container holder 38 is arranged to accommodate a medicament container 56 that in the embodiment shown is a syringe, having an injection needle 58 attached to a proximal end thereof and a stopper 60 of resilient material that is movable inside the tubular body of the medicament container 56.

Figure 15:
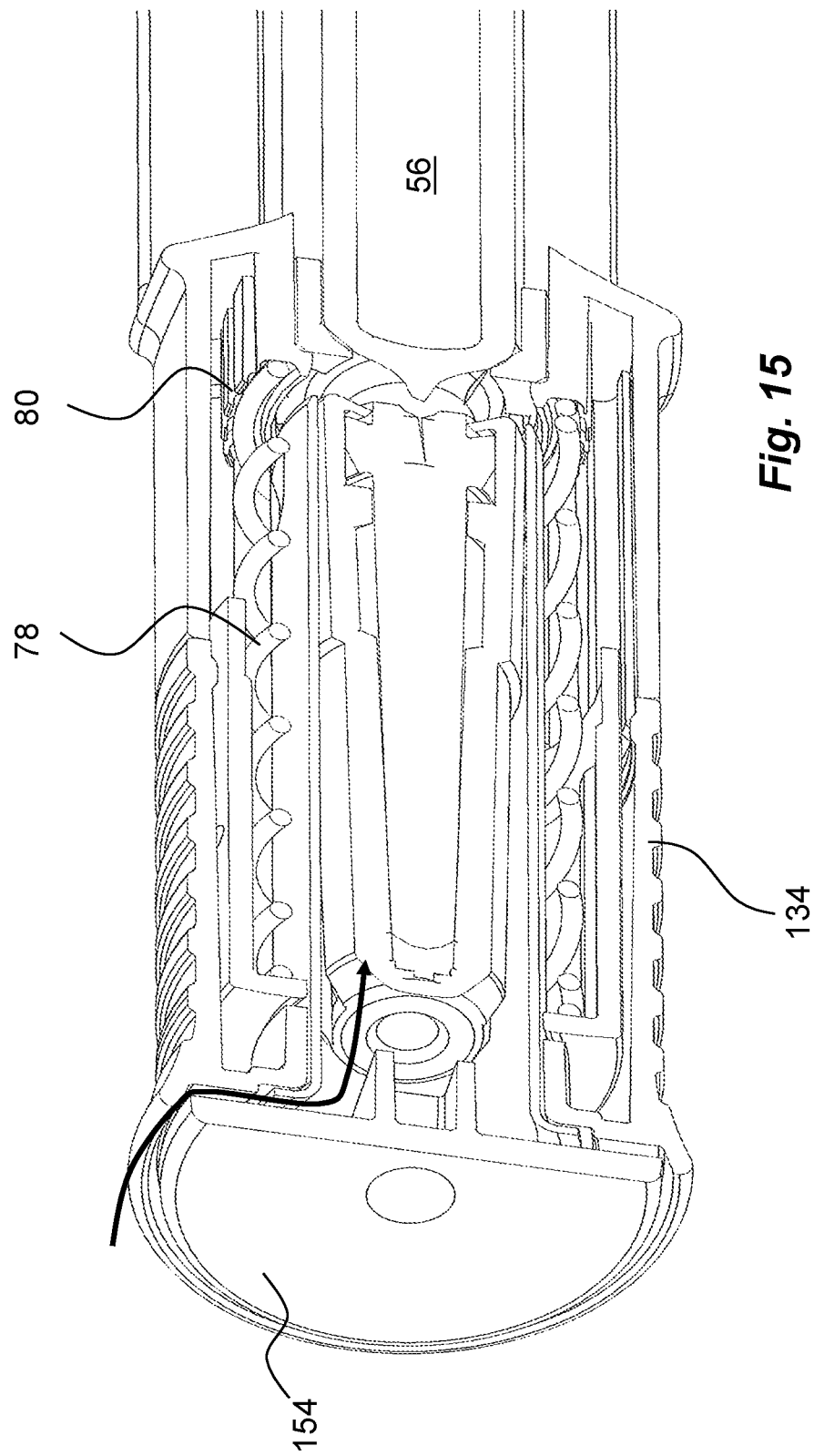
FIG. 15 is a detailed view of components comprised in the medicament delivery device of FIG. 1.

The medicament delivery device (10) further comprises a medicament delivery member guard 62, FIGS. 1 and 7. The medicament delivery member guard 62 comprises a proximal generally tubular body 64 provided with a central passage 66 in a transversal end wall 68. Two oppositely positioned arms 70 are arranged to the distal area of the body 64 and extending in the distal direction. The arms 70 are arranged with longitudinal slits 72 which are to cooperate with the longitudinal ribs 30 of the interior of the housing. At the distal end of the arms 70, outwardly directed ledges 74 are provided. Further on the inner surface of the arms 70, inwardly directed protrusions 76 are arranged, the function of which will be described. A medicament delivery member guard spring 78 is further arranged between a distally directed surface of the transversal end wall 68 of the medicament delivery member guard 62 and a proximally directed surface of the wall 16. In this regards, proximally directed support protrusions 80, FIGS. 5 and 15, are provided on the wall 16 for supporting the medicament delivery member guard spring 78 and preventing it from accidentally interacting with the arms 70 of the medicament delivery member guard 62.

Figure 8:
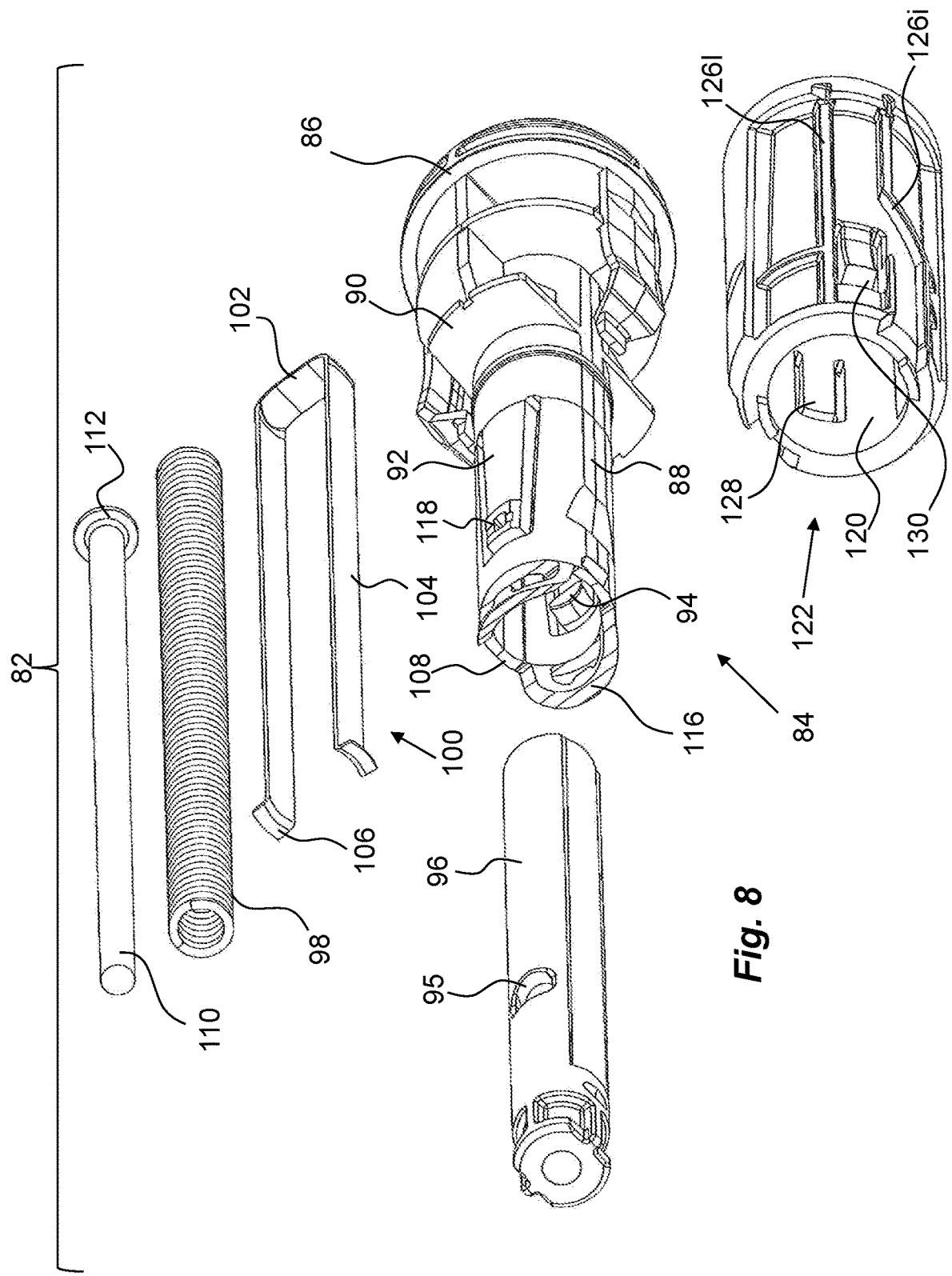
FIG. 8 is a detailed view of components comprised in the medicament delivery device of FIG. 1.

The medicament delivery device shown also comprises a power pack or drive unit 82. The power pack 82 comprises an actuator 84 provided with a distal portion forming an end cap 86 of the medicament delivery device when the actuator is connected to the housing. The proximal part of the actuator 84 comprising a generally elongated tubular body 88. A transversal support surface 90 is arranged in the area between the end cap 86 and the body 88, which support surface 90 is designed to cooperate with the ledges 36 of the tongues 34 on the housing 12 for locking the actuator 84 to the housing 12 as seen in FIGS. 1 and 8. The body 88 is further arranged with proximally directed arms 92 that are flexible in a generally radial direction. The free ends of the arms 92 are provided with inwardly directed protrusions 94. These inwardly directed protrusions 94 are arranged to fit into and cooperate with recesses 95 in an elongated plunger rod 96, which plunger rod 96 is intended to fit into and be coaxial with the body 88 of the actuator 84.

Further, a drive spring 98 is arranged inside the plunger rod 96 as well as a bracket 100 having a transversal distal part 102 and two proximally extending arms 104 on either side of, and outside, the drive spring 98. The ends of the arms 104 are arranged with outwardly extending ledges 106, which ledges 106 are to be in contact with proximally directed edge surfaces 108 of the body 88 of the actuator 84. Inside the drive spring 98 a guide rod 110 is arranged, provided with a disk 112 at its distal end. The drive spring 98 is thus arranged between a proximal end wall 114 of the plunger rod 96 and the transversal distal part 102 of the bracket 100 via the disk 112 of the guide rod 110, FIG. 3. Further, at the proximal end of the body 88, arc-shaped support elements 116 are arranged, which are flexible in the generally longitudinal direction and are intended to be in contact and support the medicament container 56 in the distal direction.

Moreover, the free ends of the arms 92 of the body 88 are arranged with outwardly directed protrusions 118 that are intended to cooperate with inner surfaces 120 of a generally tubular rotator 122 that is arranged outside and coaxial with the body 88 of the actuator 84. The inner surface 120 of the rotator 122 is arranged with longitudinally extending grooves 124, FIG. 9, the function of which will be described below. The outer surface of the rotator 122 is arranged with guide ledges or ribs 126, where some are extending in the longitudinal direction 126*l* and some are inclined 126*i* in relation to the longitudinal direction as will be explained. Adjacent one longitudinal guide rib 126*l*, a proximally directed tongue 128 is arranged, which tongue 128 is flexible in the generally radial direction, and where the free end of the tongue 128 is arranged with an outwardly directed, wedge-shaped, protrusion 130.

The medicament delivery device is further arranged with a safety cap 132, FIGS. 1, 2 and 10, comprising a generally tubular body 134 having a distal passage 136. In order to provide a good fit between the safety cap 132 and the medicament delivery device 10, the inner surface of the body 134 of the safety cap 132 may be arranged with a circumferential ledge 138, which ledge 138 is arranged to interact with protrusions 140, FIGS. 11 and 14, on the outer surface of the body 64 of the medicament delivery member guard 62 as seen in FIG. 7. The body 134 of the safety cap 132 is further arranged with a distally directed end surface 135, FIGS. 11 and 14, that acts as an abutment surface against a proximally directed end surface 137, FIGS. 4 and 14, of the housing 12, which end surface 137 also acts as an abutment surface such that the surfaces 135, 137 provide a specific position of the safety cap 132 when mounted onto the medicament delivery device.

Figure 12:
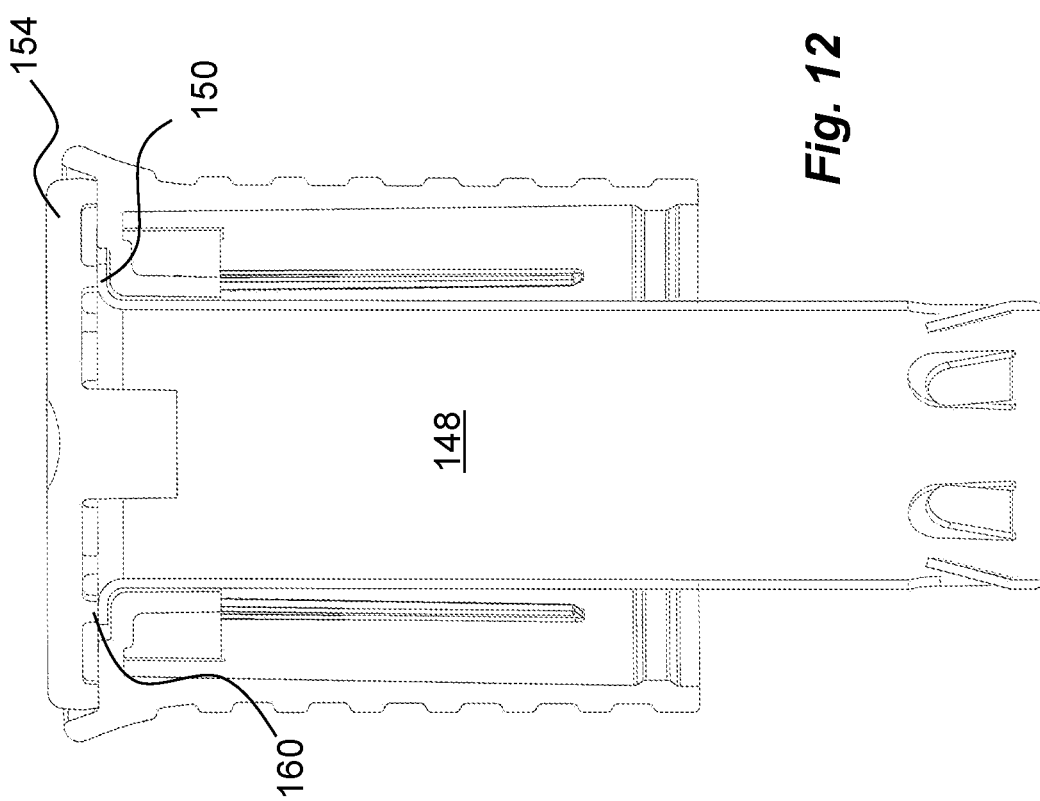
FIG. 12 is a detailed view of components comprised in the medicament delivery device of FIG. 1.

Moreover, the body 134 of the safety cap 132 is arranged with a proximal end wall 142, which end wall 142 is arranged with a central circular passage 144. Radially outside the central passage 144 are two oppositely positioned arc-shaped openings 146. A generally tubular medicament delivery member shield remover 148 is to be positioned in the central passage 144 of the end wall 142, wherein the medicament delivery member shield remover 148 will extend into the body 134 of the safety cap 132. The proximal end of the medicament delivery member shield remover 148 is arranged with an outwardly extending ledge 150, which ledge 150 is arranged to be seated in a recess 152 in the end wall 142 of the body 134. The medicament delivery member shield remover 148 is held in place in this position by an end lid 154. The end lid 154 is arranged with distally directed arc-shaped arms 156, provided with radially outwardly directed ledges 158, wherein the arms 156 are designed to fit into the arc-shaped openings 146 of the body 134 and the ledges 158 will snap around edges of the arc-shaped openings 146, locking the end lid 154 to the body 134 of the safety cap 132. The end lid 154 is further arranged with a number of distally directed protrusions or ledges 160 which are to be in contact with the ledge 150 of the medicament delivery member shield remover 148, holding it in place in the recess 152, see FIG. 12.

Figure 13:
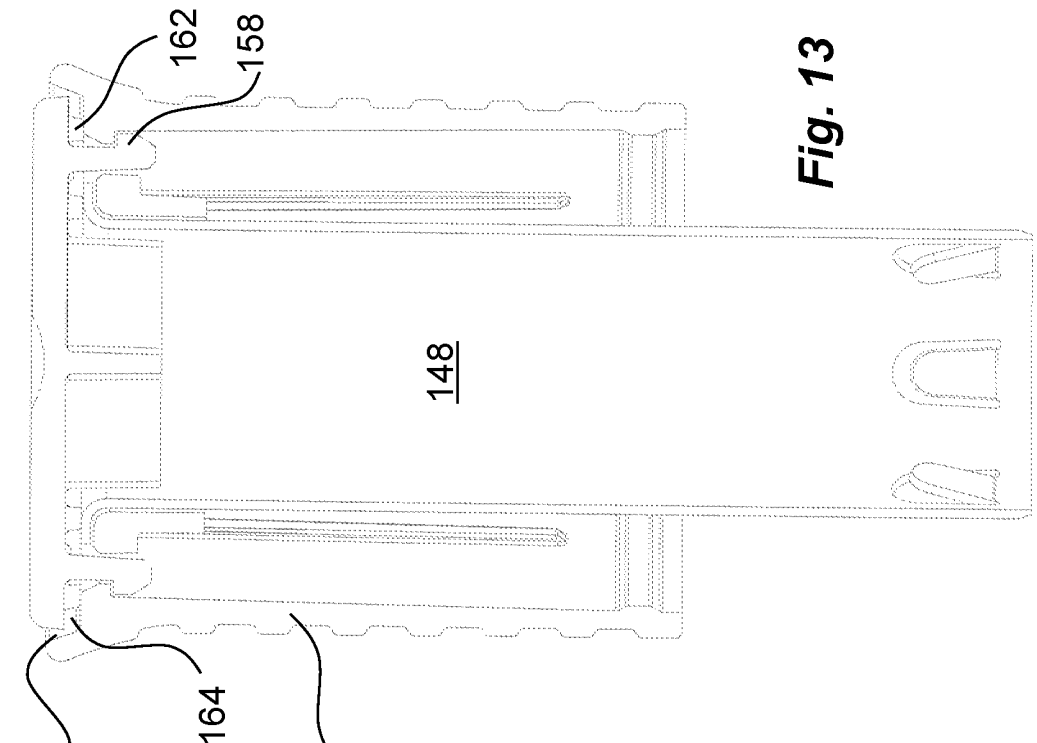
FIG. 13 is a detailed view of components comprised in the medicament delivery device of FIG. 1.

The end lid 154 is arranged with further protrusions 162 at the edge of the end lid 154 that are in contact with the end wall 142 of the body 134, acting as spacers for creating a space 164 between the body 134 and the end lid 154, FIG. 13. The diameter of the end lid 154 is further chosen such in relation to the proximal edge of the body 134 such that gaps 166 are created around the circumference. The design provides an air passage through the safety cap 132, as seen by the arrow in FIG. 15, preventing possible suffocation should a child for example put the safety cap 132 in the mouth. Moreover, the distal end of the medicament delivery member shield remover 148 is arranged with generally proximally and inwardly inclined tongues 168 that are designed to be in contact with and engage a medicament delivery member shield 170 such as a rigid needle shield or a flexible needle shield, covering the injection needle 58.

Figure 14:
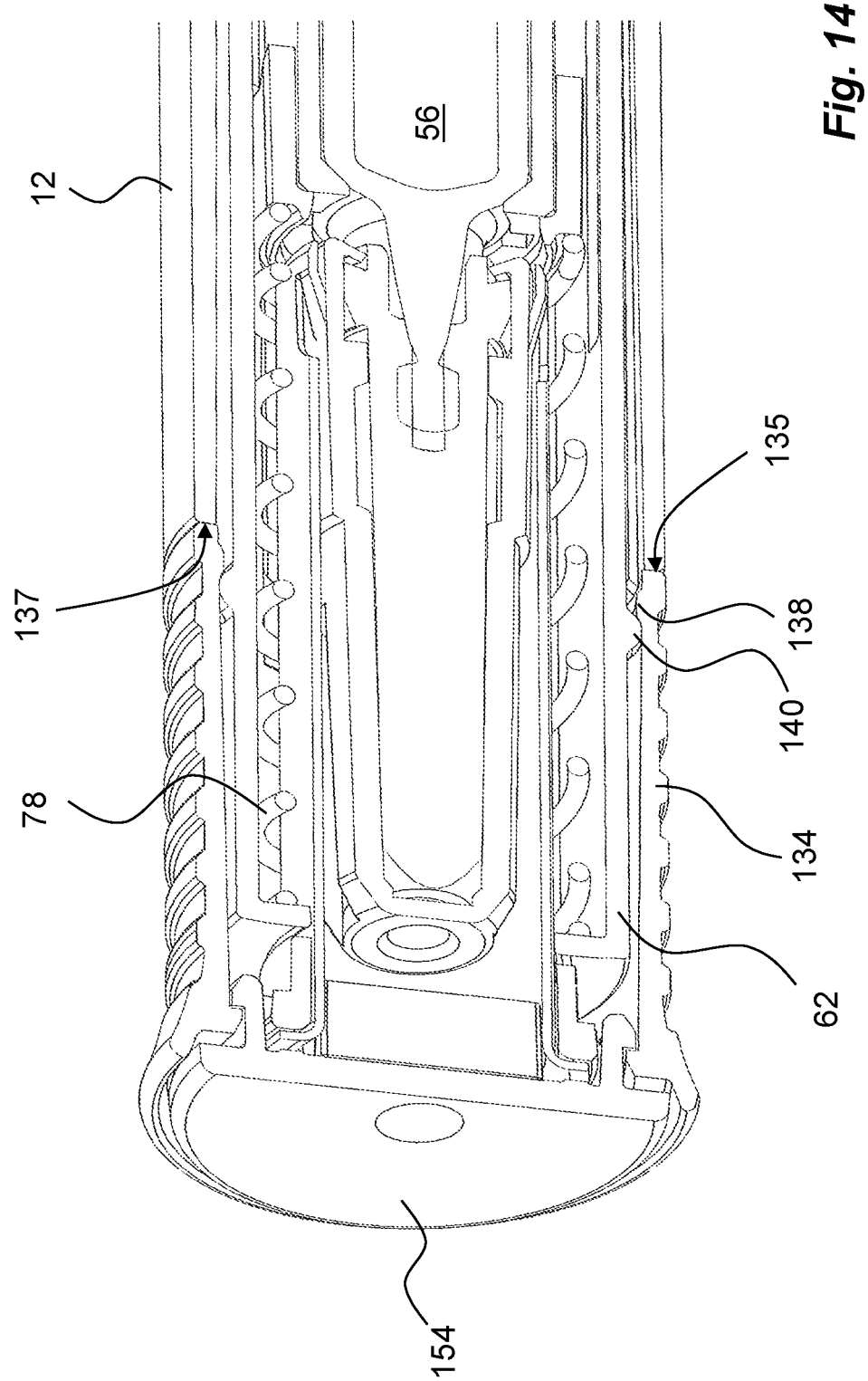
FIG. 14 is a detailed view of components comprised in the medicament delivery device of FIG. 1.

The medicament delivery device according to the drawings is intended to function as follows. The medicament delivery device is delivered to a user with the safety cap 132 attached to the proximal end of the medicament delivery device. The medicament delivery member guard 62 is in an extended position in relation to the housing 12 such that when the abutment surface 135 of the safety cap 132 is in contact with the abutment surface 137 of the housing, the circumferential ledge 138 is distally of, and in contact with, the protrusions 140 of the medicament delivery member guard 62 as seen in FIG. 14. This provides a very secure fit, reducing the risk for premature release of the safety cap 132.

The medicament delivery device (10) is generally activated by the medicament delivery member guard 62 being pushed into the housing 12 when the proximal end of the medicament delivery device is pressed against a dose delivery site, as will be described. This may happen accidentally if the medicament delivery device is dropped against a hard surface such as a floor. Now there is a risk that the medicament delivery device 10 is activated in that the medicament delivery member guard 62 may be moved in relation to the housing 12 due to the accidental impact forces, which might premature trigger the medicament delivery device. This risk is reduced and minimized in that the medicament delivery member guard 62 is held by the engagement with the safety cap 132 by the protrusions 140 interacting with the ledge 138.

When the safety cap 132 is removed, the medicament delivery member shield remover 148 grips the medicament delivery member shield 170 with its tongues 168, whereby also the medicament delivery member shield 170 is removed. The user may now press the proximal end of the medicament delivery device 10 against the dose delivery site, whereby the medicament delivery member guard 62 is pushed into the housing 12, causing a penetration by the injection needle 58. The movement of the medicament delivery member guard 62 will cause its protrusions 76 at the distal end to slide in relation to the rotator 122. When the protrusions 76 reach the inclined guide ribs 126*i* of the rotator 122, the rotator 122 will rotate in relation to the actuator 84, which in turn causes the outwardly protrusions 118 of the arms 92 of the actuator 84 to be moved in position with the longitudinal grooves 124 on the inner surface 120 of the rotator 122. The arms 92 are thereby free to move radially outwards, whereby the engagement between the inwardly directed protrusions 94 and the recesses 95 of the plunger rod 96 is removed, releasing the plunger rod 96. The plunger rod 96 is then urged in the proximal direction by the force of the drive spring 98. The plunger rod 96 will now act on and move the stopper 60 of the medicament container 56 in the proximal direction, expelling a dose of medicament through the injection needle 58. At the end of the injection sequence, the distal end of the plunger rod 96 will pass the bracket 100 whereby the arms 104 of the bracket 100 are free to move radially inwards, wherein the ledges 106 are moved out of contact with the surfaces 108 of the actuator 84. Because the distal end of the drive spring 98 is in contact with the transversal distal part 102 of the bracket 100 via the disk 112 of the guide rod 110 and since the drive spring 98 has a residual force, the bracket 100 will be forced suddenly in the distal direction until the distal end of the bracket 100 hits an end wall of the actuator 84, causing a tactile and audible signal to the user that the injection sequence is completed and that it is safe to remove the medicament delivery device from the dose delivery site.

The user can now remove the medicament delivery device 10 whereby the medicament delivery member guard 62 is pushed in the proximal direction by the medicament delivery guard spring 78. This will cause the protrusions 76 of the medicament delivery member guard 62 to move such that they come in contact with and pass the wedge-shaped protrusions 130 of the tongues 128 of the rotator 122. The passing of the protrusions 130 will cause a locking of the medicament delivery member guard 62 in the extended position, covering the injection needle 58, in turn preventing accidental injuries on the injection needle 58. The medicament delivery device can now be discarded.

Figure 18:
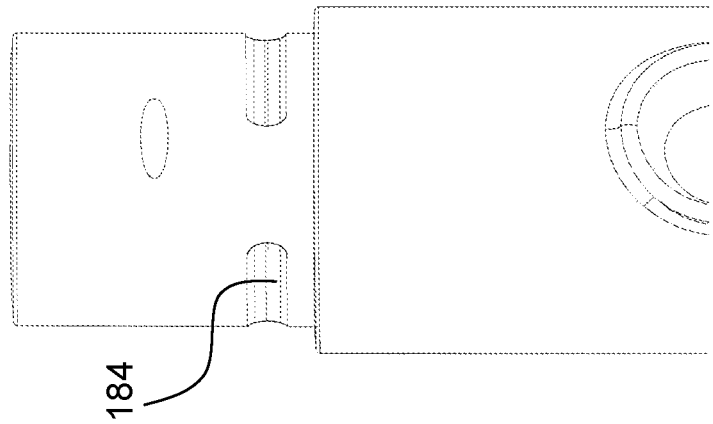
FIG. 18 is a detailed view of components comprised in the medicament delivery device of FIG. 1.
Figure 17:
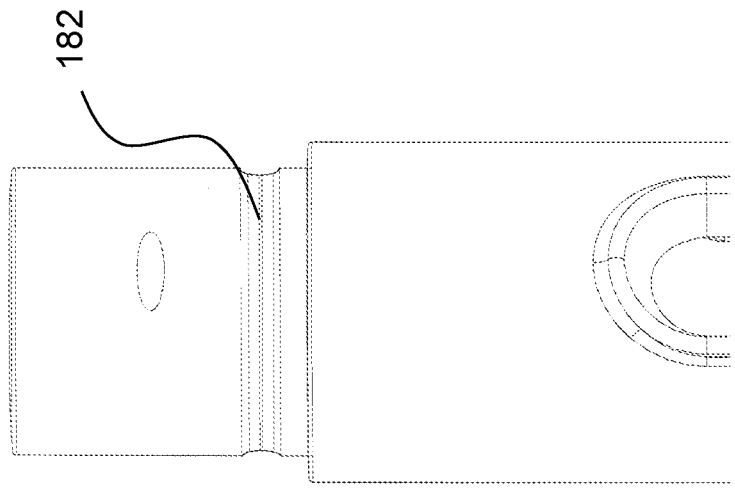
FIG. 17 is a detailed view of components comprised in the medicament delivery device of FIG. 1.
Figure 16:
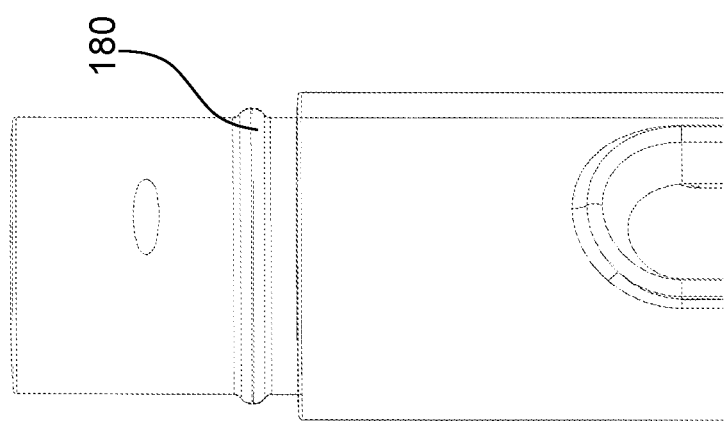
FIG. 16 is a detailed view of components comprised in the medicament delivery device of FIG. 1.
Figure 21:
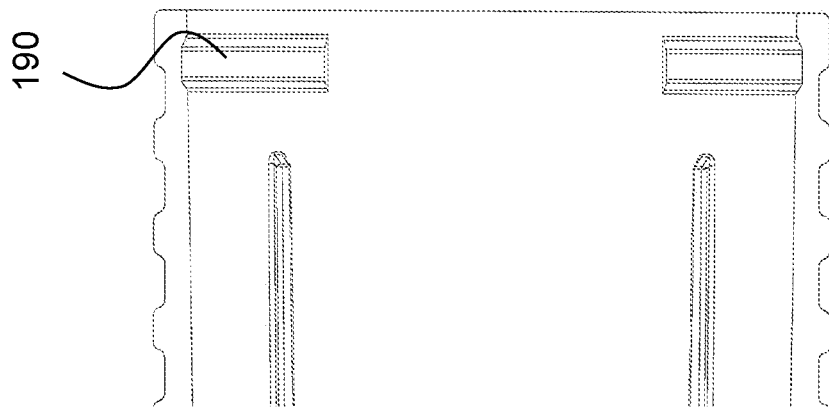
FIG. 21 is a detailed view of components comprised in the medicament delivery device of FIG. 1.
Figure 20:
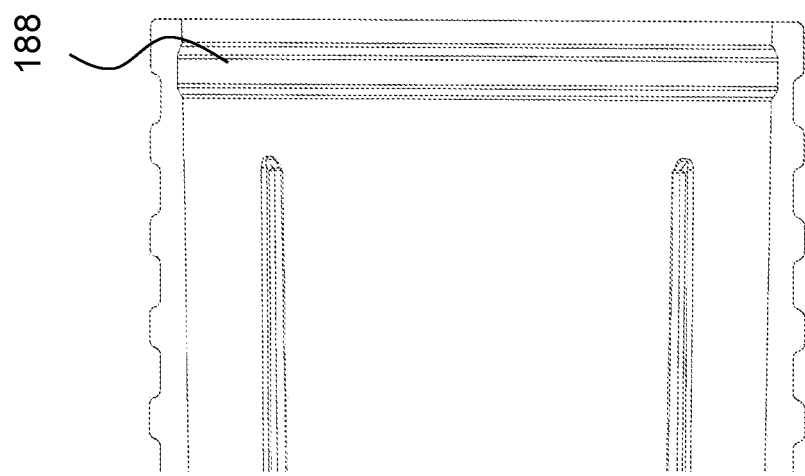
FIG. 20 is a detailed view of components comprised in the medicament delivery device of FIG. 1.
Figure 19:
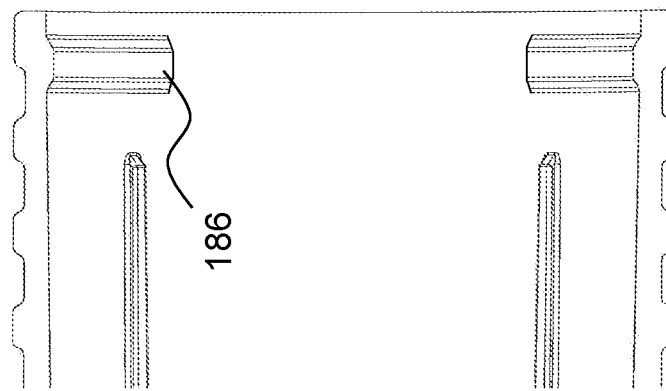
FIG. 19 is a detailed view of components comprised in the medicament delivery device of FIG. 1.

Regarding the securing of the medicament delivery member guard 62 it is to be understood that several other alternatives are feasible. Instead of discrete protrusions on the outer surface of the medicament delivery member guard 62, there could for example be a continuous protrusion 180 running along the circumference as seen in FIG. 16. As an alternative, there could be a recess in the medicament delivery member guard 62 and protrusions on the inner surface of the body of the safety cap 132. It is to be understood that the recesses in the medicament delivery member guard 62 could either be continuous 182 as seen in FIG. 17 or discrete 184 as seen in FIG. 18. As a further alternative, the protrusion on the inner surface of the safety cap 132 may be discrete 186 instead of continuous, FIG. 19. As yet an alternative there may be recesses on the inner surface of the safety cap 132, either continuous 188, FIG. 20 or discrete 190, FIG. 21. As understood there are many variants that may be combined in order to obtain the desired function of enhanced safety against accidental activation.

It is to be understood that the embodiment described above and shown in the drawings is to be regarded only as a non-limiting example that may be modified in many ways within the scope of the patent claims.

The invention claimed is:

1. A protective cap to be releasably connected to a medicament delivery device, where the protective cap comprises:
   a tubular body comprising an inner distal passage;
   a lid that attaches to a proximal end of the tubular body through a snap fit connector, wherein a diameter of the lid is chosen such in relation to a proximal edge of the tubular body that a gap is created around a circumference of the lid; and wherein the lid further comprises:
     at least two exterior protrusions to contact an end wall of the tubular body, wherein an exterior void exists between the at least two exterior protrusions, and wherein the exterior void creates a space between the tubular body and the lid; and
     at least two interior protrusions, wherein an interior void exists between the at least two interior protrusions;
   a medicament delivery member shield remover attached to the tubular body and held in position by the at least two interior protrusions of the lid, wherein the interior void creates a space between the medicament delivery member shield remover and the lid; and
   an air passage in the protective cap through which air can freely move, wherein the air passage comprises the gap, the space created by the exterior void, and the space created by the interior void.

2. The protective cap according to claim 1, wherein the snap fit connector comprises distally directed at least two arms, wherein the at least two arms are arranged with ledges, wherein the tubular body comprises at least two openings, wherein the at least two arms are designed to fit into the at least two openings of the tubular body and the ledges are configured to snap around edges of the at least two openings.

3. The protective cap according to claim 2, wherein the at least two arms are arc-shaped and the ledges are radially outwardly directed ledges, and that the at least two openings are arc-shaped.

4. The protective cap according to claim 1, wherein the end wall comprises a recess.

5. The protective cap according to claim 4, wherein the at least two interior protrusions of the lid are in contact with a ledge of the medicament delivery member shield remover, holding the lid in place in the recess in the end wall of the tubular body.

6. The protective cap according to claim 1, wherein an inner surface of the tubular body of the protective cap is arranged with a circumferential ledge.

7. A medicament delivery device comprising a generally tubular housing with a proximal end and a distal end, wherein the medicament delivery device comprises the protective cap according to claim 1.

8. The medicament delivery device according to claim 7, wherein the medicament delivery device further comprises a medicament delivery member guard.

9. The medicament delivery device according to claim 8, wherein the medicament delivery member guard comprises a proximal generally tubular body provided with a central passage in a transversal end wall and protrusions on an outer surface of the proximal generally tubular body.

10. The medicament delivery device according to claim 8, wherein a protective cap ledge is arranged to interact with protrusions on an outer surface of a body of the medicament delivery member guard.

11. The medicament delivery device according to claim 8, wherein the medicament delivery device is activated by the medicament delivery member guard being pushed into the housing when a proximal end of the medicament delivery device is pressed against a dose delivery site.

12. The medicament delivery device according to claim 8, wherein the medicament delivery member guard comprises protrusions that engage with a circumferential ledge on an inner surface of the tubular body to prevent distal axial movement of the medicament delivery member guard due to accidental impact forces, where said engagement between the protrusions and the circumferential ledge reduces a risk for premature triggering of the medicament delivery device.

13. The medicament delivery device according to claim 12, wherein when the medicament delivery member guard is in an extended position in relation to the housing, the circumferential ledge is distally of and in contact with the protrusions of the medicament delivery member guard reducing a risk for a premature release of the protective cap.

\* \* \* \* \*